(12) United States Patent
Kosiorek et al.

(10) Patent No.: US 11,207,077 B2
(45) Date of Patent: Dec. 28, 2021

(54) JUNCTIONAL HEMORRHAGE CONTROL PLATE APPARATUS, SYSTEMS, AND METHODS

(71) Applicant: ALPHAPOINTE, Kansas City, MO (US)

(72) Inventors: Christopher B. Kosiorek, La Vernia, TX (US); Esra Abir, New York, NY (US); Christian D. Reid, Concord, NC (US); Jon R. Mattson, Concord, NC (US); Christopher J. Murphy, Vass, NC (US); Corey F. Russ, Harrisburg, NC (US); Ryan Williams, Olathe, KS (US)

(73) Assignee: ALPHAPOINTE, Kansas City, MO (US)

( * ) Notice: Subject to any disclaimer, the term of this patent is extended or adjusted under 35 U.S.C. 154(b) by 191 days.

(21) Appl. No.: 16/250,896

(22) Filed: Jan. 17, 2019

(65) Prior Publication Data
US 2019/0216469 A1    Jul. 18, 2019

Related U.S. Application Data

(60) Provisional application No. 62/618,484, filed on Jan. 17, 2018.

(51) Int. Cl.
*A61B 17/132* (2006.01)
*A61B 17/12* (2006.01)
*A61B 17/00* (2006.01)

(52) U.S. Cl.
CPC .......... *A61B 17/1325* (2013.01); *A61B 2017/00477* (2013.01); *A61B 2017/12004* (2013.01)

(58) Field of Classification Search
CPC .............. A61B 17/132; A61B 17/1325; A61B 2017/00477; A61B 2017/12004; A61B 17/12; A61F 5/30
See application file for complete search history.

(56) References Cited

U.S. PATENT DOCUMENTS

| 3,570,496 | A | * | 3/1971 | Sachs ................. A61B 17/1325 |
| | | | | 606/203 |
| 5,307,811 | A | | 5/1994 | Sigwart et al. |
| 5,695,520 | A | | 12/1997 | Bruckner et al. |

(Continued)

FOREIGN PATENT DOCUMENTS

| CN | 205729433 U | 11/2016 |
| JP | 2007196018 A | 8/2007 |
| WO | 2019143855 A1 | 7/2019 |

OTHER PUBLICATIONS

International Search Report and Written Opinion Received PCT Application No. PCT/US19/14071 dated May 9, 2019, 14 pages.

*Primary Examiner* — George J Ulsh
(74) *Attorney, Agent, or Firm* — Kutak Rock LLP; Brian L. Main

(57) ABSTRACT

Apparatus, methods, and systems for junctional hemorrhage control and pelvic stabilization are provided. The hemorrhage control plate includes a baseplate and a bulbous node extending outwardly. It is positioned against a patient's body such that it aligns with an artery. It is used in connection with a tourniquet to occlude blood flow at a junctional hemorrhage site. The device includes tabs to attach to the tourniquet.

24 Claims, 4 Drawing Sheets

(56) References Cited

U.S. PATENT DOCUMENTS

| | | | | |
|---|---|---|---|---|
| 2002/0007195 A1* | 1/2002 | Wexler | .................... | A61F 13/12 |
| | | | | 606/204.15 |
| 2013/0267994 A1 | 10/2013 | Crowder et al. | | |
| 2015/0094756 A1 | 4/2015 | Kosiorek et al. | | |
| 2016/0095605 A1* | 4/2016 | Maris | ................. | A61B 17/1327 |
| | | | | 606/201 |
| 2016/0287262 A1* | 10/2016 | Kirchner | ............ | A61B 17/1322 |

* cited by examiner

JUNCTIONAL HEMORRHAGE CONTROL PLATE APPARATUS, SYSTEMS, AND METHODS

CROSS-REFERENCE TO RELATED APPLICATIONS

This application claims priority pursuant to 35 U.S.C. 119(e) to U.S. Provisional Patent Application Ser. No. 62/618,484, entitled "JUNCTIONAL HEMORRHAGE CONTROL PLATE APPARATUS, SYSTEMS, AND METHODS," filed Jan. 17, 2018, the entire disclosure of which is incorporated herein by reference.

FIELD

The present invention relates generally to apparatuses and related systems and methods configured to control blood loss in a patient. More specifically, the present invention is concerned with a small, lightweight, easy-to-use device that can be used to apply direct pressure to a major artery such as the femoral artery or axillary artery.

BACKGROUND

Approximately 80 percent of potentially survivable casualties on today's battlefield nevertheless result in mortality due to uncontrolled hemorrhage. Devices that control hemorrhage on the battlefield early in the continuum of care may likely increase the survivability of combat casualties. The present inventive concept has been developed and intended to be carried in the Individual First Aid Kit (IFAK), and Combat Lifesaver (CLS) bags for temporary control of junctional hemorrhage. In some embodiments, the present inventive concept is used in conjunction with a tourniquet such as described in U.S. Pat. Pub. No. US20150094756 to control hemorrhage in compressible, non-tourniquetable regions.

The Wake Forest School of Medicine human cadaver hemostasis model was used to test the efficacy of the present inventive concept. This testing platform uses a pulsatile peristaltic pump to produce realistic constant blood flow within the arteries of a fresh unembalmed human cadaver. Testing hemostatic devices and procedures using intact fresh human tissue has some advantages over alternative live tissue models when a mechanical device is employed to reduce arterial flow rates.

Authentic human anatomy is an important requirement for validating the efficacy of hemorrhage control devices when an external control device is applied to control flow in the external iliac artery at or above the inguinal ligament where peripheral limb tourniquet application cannot be used. In this feasibility study, one fresh human cadaver was used with peristaltic tubing inserted and sealed within the thoracic aorta. An external peristaltic pump was used to deliver fluid through arteries in the descending abdomen, pelvis and limbs of the cadaver with a constant peristaltic speed and constant arterial flow rate consistent with physiological levels. The right popliteal arteries were cut in order to observe dynamic changes in downstream arterial flow rates from fluid pumped through the thigh before, during and after the application of hemorrhage control devices with constant peristaltic pumping. Successful application was measured by arresting of flow through the external iliac artery by observing the flow rate at the exposed popliteal artery.

The human hemostatic testing model developed at the Wake Forest School of Medicine was used to demonstrate the capacity of the present inventive concept to stop arterial flow when applied to the external iliac artery. The present inventive concept completely stopped blood flow and arterial pressure with minimal turns of the tourniquet windlass when the device was applied to the surface of the cadaver just above the inguinal ligament. The present inventive concept controlled arterial flow through the external iliac in 40 tests on 4 cadaver models.

The present inventive concept effectively stopped flow in the external iliac artery. It is configured to control hemorrhage in junctional regions.

SUMMARY

The present inventive concept comprises a bulbous node extending outwardly away from a base plate. The bulbous node includes a convex surface that is configured to be position against a patient's body. When the bulbous node is placed on a patient's body aligned with an artery and pressure is applied, the convex surface applies pressure directly on the patient's artery, preferably sufficient to stop blood flow or otherwise control hemorrhage. In some embodiments, the present inventive concept is formed of a strong plastic material. In other embodiments, it is formed of metal. In some embodiments, the plate includes a tab on opposite ends. In some embodiments, the opposing tabs are sized and shaped to mate with corresponding slots in the carriage of the tactical mechanical tourniquet disclosed in U.S. Pat. Pub. No. US20150094756. In some embodiments, insertion of the tabs into the slots creates a bend in the base plate creating an arc away from the carriage and toward the patient's body, which provides for an increase in strength and rigidity and allows for use across a larger patient population.

The present inventive concept provides for mechanical hemorrhage control. External environmental changes such as temperature changes or changes in barometric pressure do not affect the functionality or use of the present inventive concept.

The present inventive concept is used for junctional hemorrhage control on upper or lower extremities. Two junctional hemorrhage control plates, one on each femoral artery, are used simultaneously to stop blood flow in the event of lower extremity bilateral amputation. The present inventive concept is used to cease radial pulse in an upper extremity. The present inventive concept is used to cease popliteal pulse and/or tibialis posterior pulse in a lower extremity.

Current clinical practice guidelines strongly recommend the use of a pelvic stabilizing device in patients who require junctional hemorrhage control in the inguinal areas. The mechanisms of injury that create the conditions requiring junctional hemorrhage control often create secondary injuries that are unseen to the naked eye. Pelvic stabilization devices serve to both manage patient comfort and minimize exacerbation of any underlying musculoskeletal injuries. To meet the generally acceptable criteria for pelvic stabilization, the device should have a minimum width of 2 inches and secure circumferentially around the pelvic girdle.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION

Figure 1:
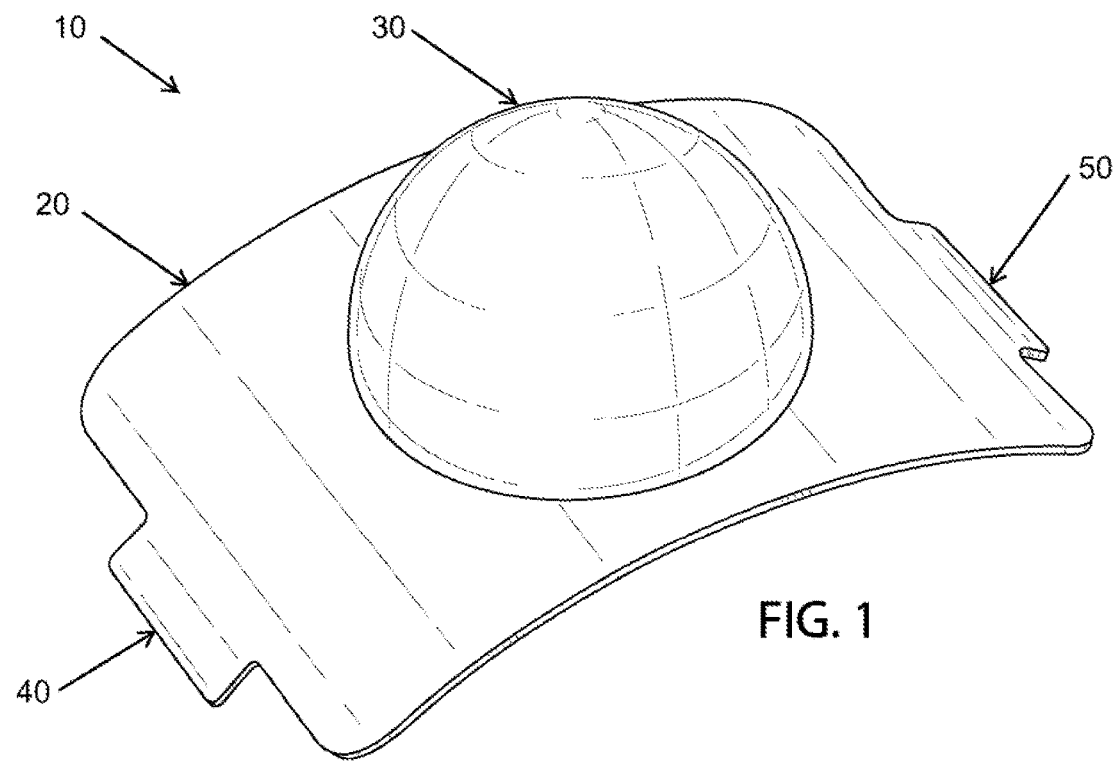
FIG. 1 is a top perspective view of an embodiment of the present invention.
Figure 2:
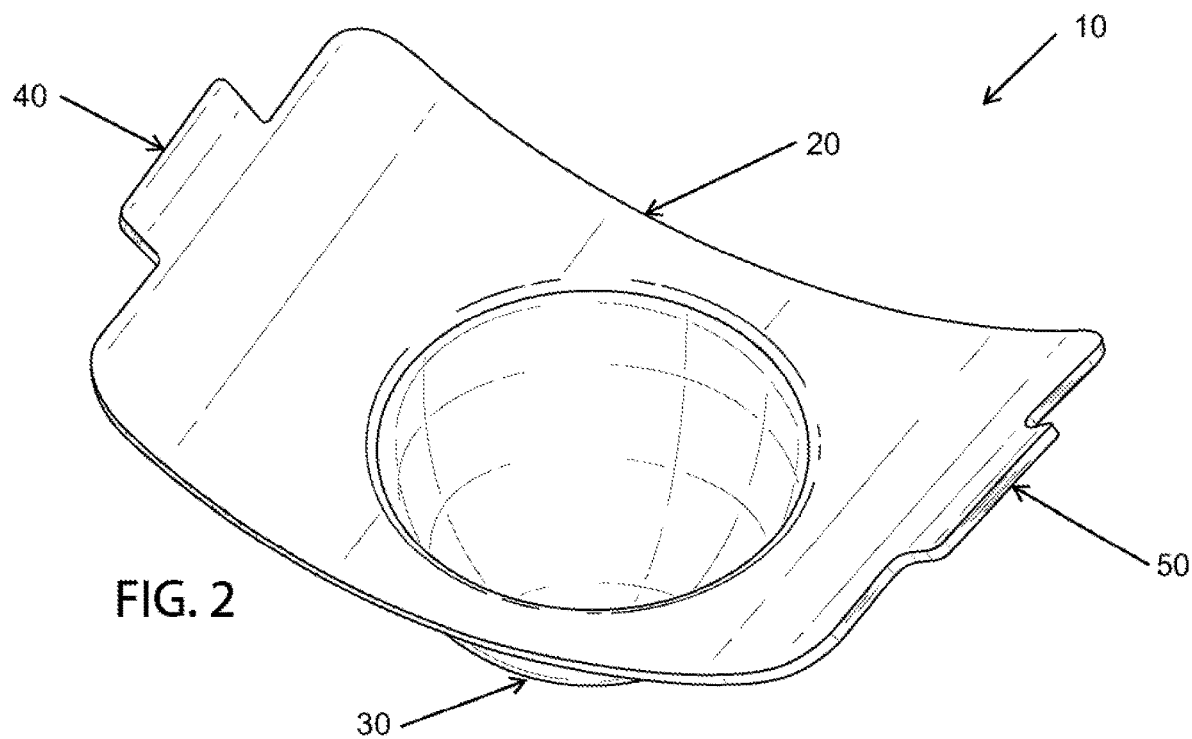
FIG. 2 is a bottom perspective view of the embodiment shown in FIG. 1.

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

The present inventive concept is directed to a hemorrhage control plate apparatus, systems of tourniquets and hemorrhage control plates, and methods of use. Referring to FIGS. 1 through 8, various embodiments of the present inventive concept are shown. In some embodiments, the present inventive concept is a hemorrhage control plate apparatus 10. The hemorrhage control plate 10 includes a baseplate 20 and a bulbous node 30 extending outwardly from the baseplate 20. In some embodiments, the bulbous node 30 is a semispherical or otherwise-shaped protrusion. In some embodiments, the bulbous node 30 includes a convex surface. In some embodiments, the bulbous node 30 is hollow. In some embodiments, the bulbous node 30 is configured to be positioned against a patient's body such that the bulbous node 30 aligns with an artery associated with the patient's body. In some embodiments, the hemorrhage control plate 10 is made of a plastic material. In some embodiments, the hemorrhage control plate 10 is made of a metal material.

In some embodiments, the hemorrhage control plate 10 includes a first insert tab 40 positioned at a first end of the baseplate 20. In some embodiments, the hemorrhage control plate 10 includes a second insert tab 50 positioned at a second end of the baseplate 20. In some embodiments, the first insert tab 40 is positioned opposite the second insert tab 50. Or in other words, the first end of the baseplate 20 is opposite the second end of the baseplate 20.

Figure 3:
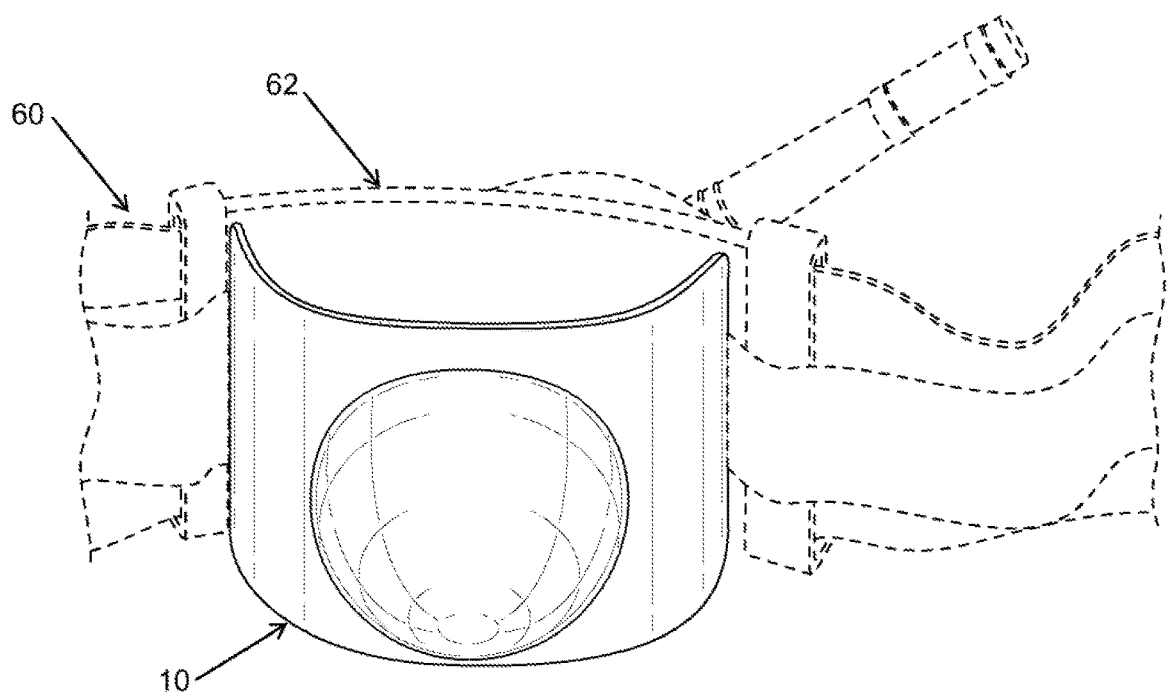
FIG. 3 is a perspective view of the embodiment shown in FIG. 1, with tourniquet shown in broken lines.
Figure 4:
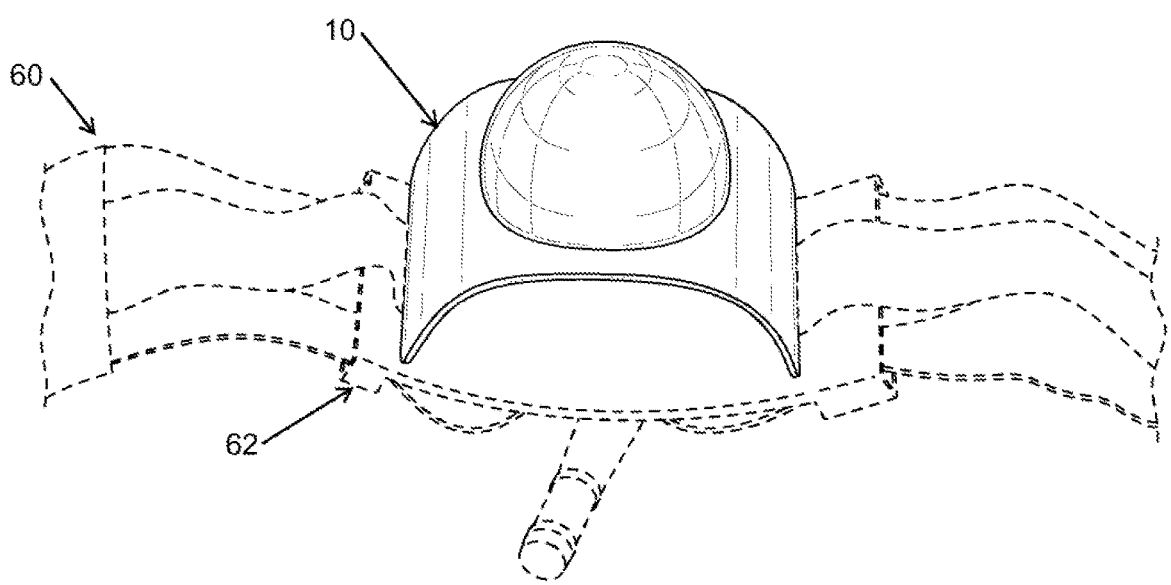
FIG. 4 is a perspective view of the embodiment shown in FIG. 1, with tourniquet shown in broken lines.
Figure 8:
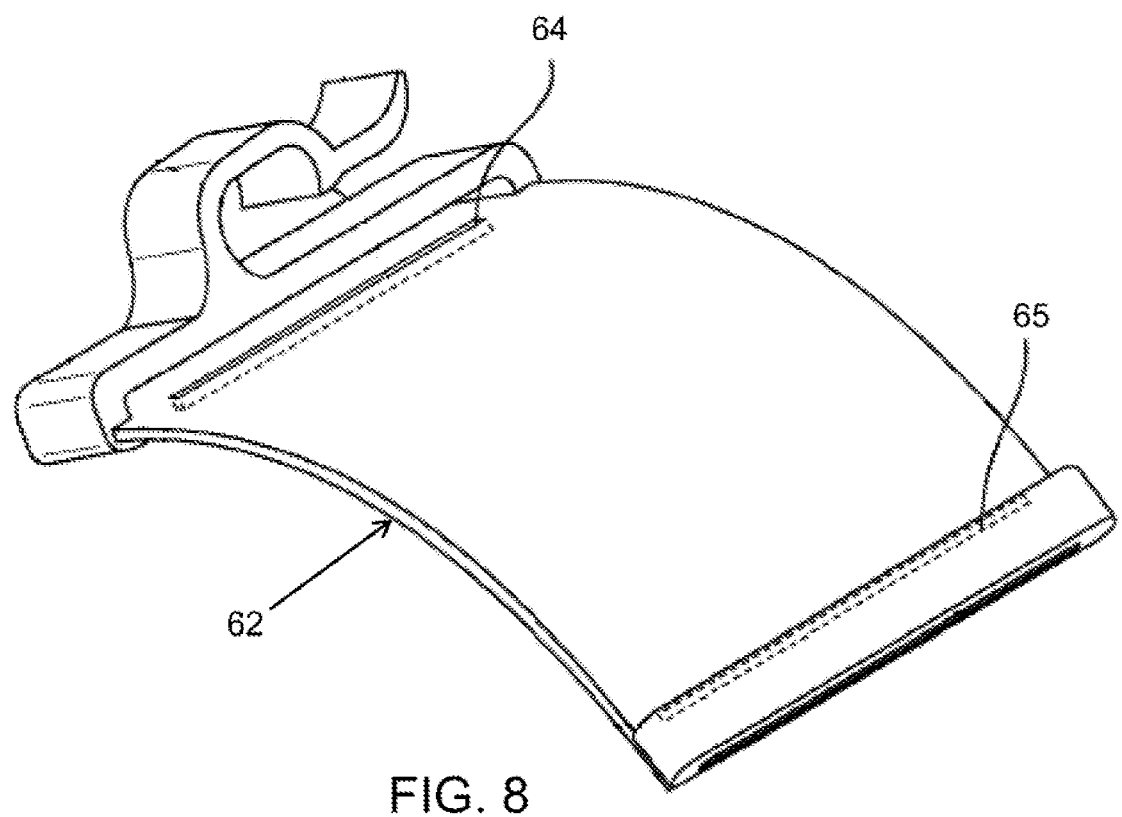
FIG. 8 is a perspective view of a carriage of the tourniquet of FIG. 3.

Referring to FIGS. 3, 4, and 8, in some embodiments, the hemorrhage control plate 10 is configured to be attached to a tourniquet 60 in any manner now known or later developed. In some embodiments, the baseplate 20 is configured to be attached to a tourniquet 60. In some embodiments, the first insert tab 40 is configured to mate with a corresponding first slot 64 in the tourniquet 60, such as a slot defined by a carriage 62 of the tourniquet 60. In some embodiments, the second insert tab 50 is configured to mate with a corresponding second slot 65 in the tourniquet 60, such as a slot defined by a carriage 62 of the tourniquet 60. In some embodiments, the first insert tab 40 is configured to mate with a corresponding first slot 64 in the tourniquet and also the second insert tab 50 is configured to mate with a corresponding second slot 65 in the tourniquet 60.

Figure 5:
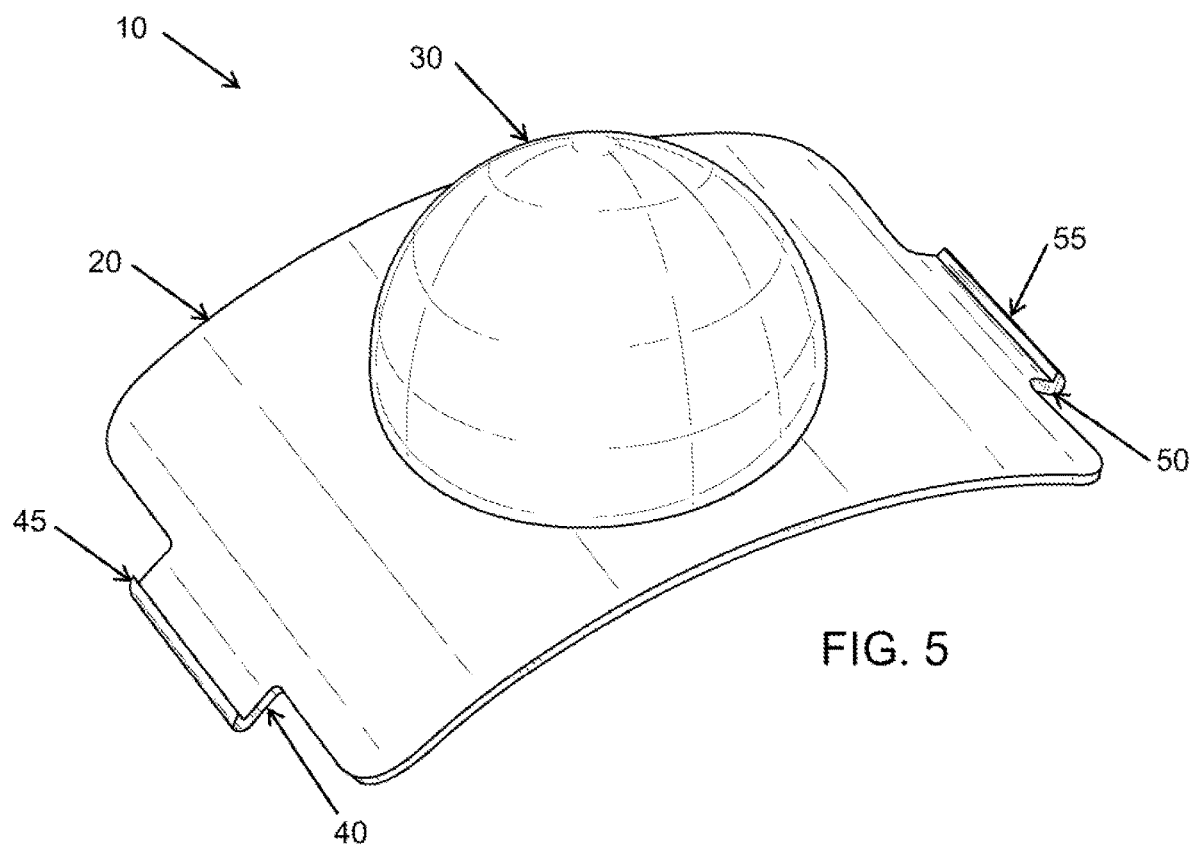
FIG. 5 is a top perspective view of an embodiment of the present invention.
Figure 6:
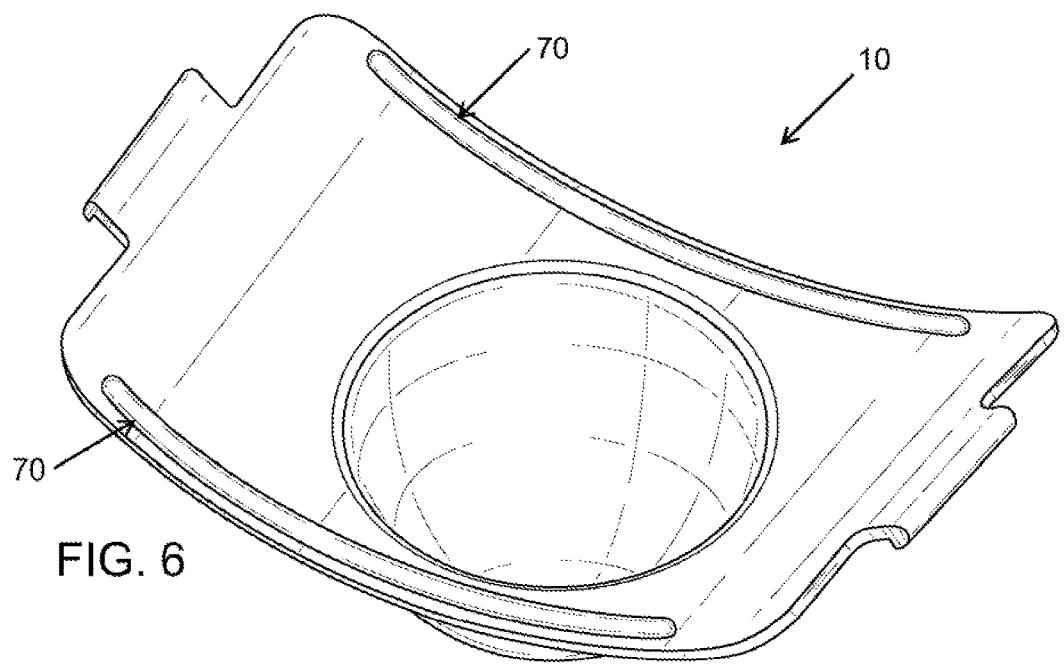
FIG. 6 is a bottom perspective view of the embodiment shown in FIG. 5.
Figure 7:
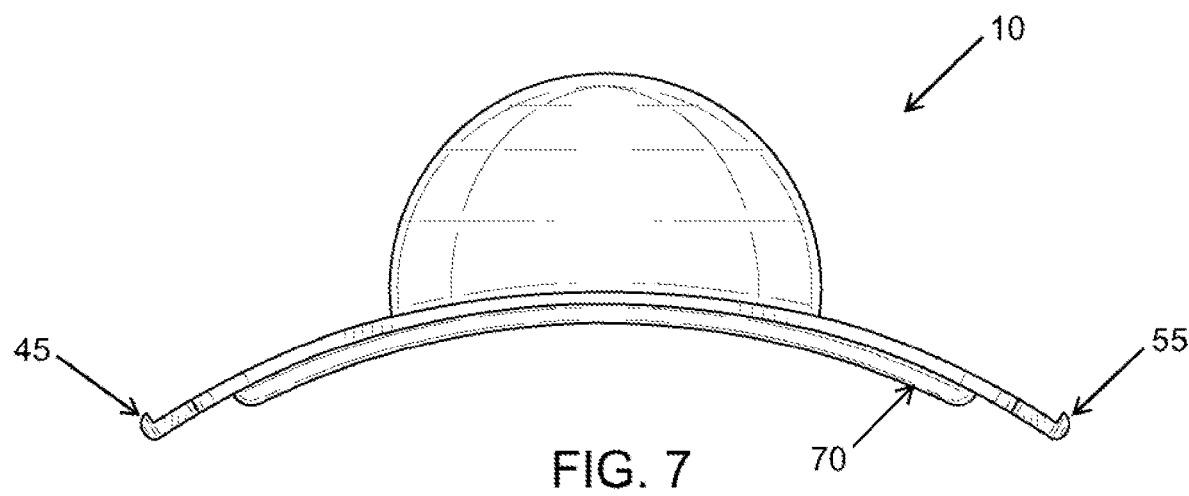
FIG. 7 is a left-side view of the embodiment shown in FIG. 5, the right-side view being a mirror image.

Referring to FIGS. 5 through 7, in some embodiments, at least one of the insert tabs 40 or 50 includes a locking end spur 45 or 55. The locking end spur 45 or 55 securely attaches the baseplate 20 to the tourniquet 60 to hold the hemorrhage control plate 10 in place, so the insert tabs 40 or 50 do not inadvertently release from corresponding slots 64 and 65.

In some embodiments, the baseplate 20 also includes one or more reinforcing rib 70, which may also be referred to as a truss or buttress. In some embodiments, the baseplate 20 includes two reinforcing ribs 70, each configured to extend lengthwise along the long axis of the hemorrhage control plate 10. In some embodiments, the reinforcing rib 70 is located near the side edge of the baseplate 20. In some embodiments, the reinforcing rib 70 is configured to be aligned in parallel with the length of the tourniquet 60 when the hemorrhage control plate 10 is attached to the tourniquet 60. The one or more reinforcing rib 70 provides stronger structural integrity when the baseplate 20 is bent in an arcuate manner.

Referring to FIGS. 3, 4, and 8, in some embodiments, the baseplate 20 is configured to bend temporarily and become arcuate when the baseplate 20 is attached to the tourniquet. In some embodiments, the baseplate 20 is configured to bend temporarily and become arcuate when the first insert tab 40 is mated with the corresponding first slot 64 of the tourniquet 60 and the second insert tab 50 is mated with the corresponding second slot 65 of the tourniquet 60. In some embodiments, the bulbous node 30 is configured to be positioned against a patient's body such that the bulbous node 30 aligns with an artery associated with said patient's body. In some embodiments, the bulbous node 30 is configured to apply pressure on the patient's artery when the tourniquet 60 is tightened. In some embodiments, the bulbous node 30 is configured to maintain pressure on the patient's artery when the tourniquet 60 is tightened.

The present inventive concept also includes various methods of use. In some embodiments, the method of use of a hemorrhage control plate 10 includes positioning at least one hemorrhage control plate 10 against a patient's body, such that a bulbous node 30 extending outwardly from a baseplate 20 of the hemorrhage control plate 10 is aligned with a corresponding artery associated with the patient's body. In some embodiments, pressure is applied and/or maintained to the hemorrhage control plate 10, such that the bulbous node 30 applies and/or maintains pressure on the corresponding artery. In some embodiments, the methods of use also include attaching the hemorrhage control plate 10 to a tourniquet 60. In some embodiments, the step of attaching the hemorrhage control plate 10 to a tourniquet 60 includes mating the first insert tab 40 with the corresponding first slot 64 in the tourniquet 60 and mating the second insert tab 50 with the corresponding second slot 65 in the tourniquet 60. In some embodiments, the method also includes bending, temporarily, the baseplate 20 such that it becomes arcuate when the insert tabs 40 and 50 are mated with their respective corresponding slots 64 and 65. In some embodiments, the method also includes tightening the tourniquet 60 to apply and/or maintain pressure to the hemorrhage control plate 10, which also applies and/or maintains pressure at the bulbous node 30 to the corresponding artery. In some embodiments, at least one of the insert tabs, preferably both, includes a locking end spur. In some embodiments, the method also includes locking the locking end spur of the first or second insert tab(s) into the corresponding first or second slot(s), respectively.

Sometimes, as the tourniquet 60 is tightened, the hemorrhage control plate 10 tends to roll such that hemorrhage control plate 10 is no longer properly aligned with the artery. In some embodiments, the baseplate 20 has two sides opposite one another and positioned between the two ends and at least one of these two sides includes a protrusion configured to reduce, mitigate, or otherwise eliminate this type of roll.

The present inventive concept also includes various tourniquet and hemorrhage control plate systems. In some embodiments, the system includes a tourniquet 60 configured to receive a hemorrhage control plate 10. The hemorrhage control plate 10 includes a baseplate 20 and a bulbous node 30 extending outwardly from the baseplate 30. The bulbous node 30 is configured to be positioned against a patient's body such that the bulbous node 30 aligns with an artery associated with the patient's body. In some embodiments, the hemorrhage control plate 10 is made of a plastic material. In some embodiments, the hemorrhage control plate 10 is made of a metal material. In some embodiments, the system is configured such that the first insert tab 40 is positioned at the first end of the baseplate 20 and the second insert tab 50 is positioned at the second end of the baseplate 20. In some embodiments, the first insert tab 40 is configured to mate with the corresponding first slot 64 in the tourniquet 60 and the second insert tab 50 is configured to mate with the corresponding second slot 65 in the tourniquet 60. In some embodiments, the baseplate 20 is configured to bend, temporarily, and become arcuate when the first and second insert tabs 40 and 50 are mated with the corresponding first and second slots 64 and 65 in the tourniquet 60. In some embodiments, the tourniquet 60 is tightened to apply pressure to the hemorrhage control plate 10, which also applies pressure at the bulbous node 30 to the corresponding artery.

While the present general inventive concept has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

It is also to be understood that the following claims are intended to cover all of the generic and specific features of the invention herein described, and all statements of the scope of the invention which, as a matter of language, might be said to fall there between. Hence, the proper scope of the present general inventive concept should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. A hemorrhage control plate comprising:
 a baseplate;
 a bulbous node extending outwardly from said baseplate; and
 a first insert tab positioned at a first end of said baseplate, wherein said first insert tab is configured to mate with a corresponding first slot in a tourniquet.

2. The hemorrhage control plate of claim 1, wherein said bulbous node is configured to be positioned against a patient's body such that said bulbous node aligns with an artery associated with said patient's body.

3. The hemorrhage control plate of claim 1, wherein said baseplate is configured to be attached to a tourniquet.

4. The hemorrhage control plate of claim 1, further comprising a second insert tab positioned at a second end of said baseplate, said second end opposite said first end.

5. The hemorrhage control plate of claim 1, wherein said first insert tab is configured to mate with a corresponding first slot in a tourniquet and said second insert tab is configured to mate with a corresponding second slot in the tourniquet.

6. The hemorrhage control plate of claim 5, wherein at least one of the first insert tab and the second insert tab further comprises a locking end spur.

7. The hemorrhage control plate of claim 5, wherein the baseplate is configured to bend temporarily and become arcuate when said first and second insert tabs are mated with said corresponding first and second slots in the tourniquet.

8. The hemorrhage control plate of claim 1, wherein the baseplate further comprises two opposing sides and at least one side having a protrusion.

9. A hemorrhage control plate comprising:
 a baseplate; and
 a bulbous node extending outwardly from said baseplate, wherein said baseplate is configured to be attached to a tourniquet, and
 wherein the baseplate is configured to bend temporarily and become arcuate when the baseplate is attached to the tourniquet.

10. The hemorrhage control plate of claim 9, wherein said bulbous node is configured to be positioned against a patient's body such that said bulbous node aligns with an artery associated with said patient's body; and said bulbous node is configured to apply pressure on said artery when the tourniquet is tightened.

11. The hemorrhage control plate of claim 10, wherein said bulbous node is configured to maintain pressure on said artery when the tourniquet is tightened.

12. The hemorrhage control plate of claim 9, wherein the baseplate further comprises one or more reinforcing rib.

13. A method of use of a hemorrhage control plate, the method comprising:

positioning at least one of the hemorrhage control plate against a patient's body such that a bulbous node extending outwardly from a baseplate of said at least one hemorrhage control plate is aligned with a corresponding artery associated with said patient's body;

applying pressure to said at least one hemorrhage control plate, such that said bulbous node applies pressure on said corresponding artery;

comprising maintaining pressure to said at least one hemorrhage control plate, such that said bulbous node maintains pressure on said corresponding artery; and attaching said at least one hemorrhage control plate to a tourniquet, wherein the step of attaching said at least one hemorrhage control plate to a tourniquet comprises:

mating a first insert tab positioned at a first end of said baseplate with a corresponding first slot in the tourniquet; and mating a second insert tab positioned at a second end of said baseplate with a corresponding second slot in the tourniquet, said second end of said baseplate being opposite of said first end.

14. The method of claim 13, wherein at least one of the first insert tab or the second insert tab further comprises a locking end spur and at least one of said steps of mating a first insert tab with a corresponding first slot or mating a second insert tab with a corresponding second slot further comprises locking the locking end spur of said at least one of the first insert tab or the second insert tab into said corresponding first slot or corresponding second slot.

15. A method of use of a hemorrhage control plate, the method comprising:

positioning at least one of the hemorrhage control plate against a patient's body such that a bulbous node extending outwardly from a baseplate of said at least one hemorrhage control plate is aligned with a corresponding artery associated with said patient's body;

applying pressure to said at least one hemorrhage control plate, such that said bulbous node applies pressure on said corresponding artery;

comprising maintaining pressure to said at least one hemorrhage control plate, such that said bulbous node maintains pressure on said corresponding artery;

attaching said at least one hemorrhage control plate to a tourniquet; and bending temporarily the baseplate such that the baseplate becomes arcuate when the hemorrhage control plate is attached to the tourniquet.

16. The method of claim 15, further comprising:

tightening the tourniquet to apply pressure to said at least one hemorrhage control plate.

17. The method of claim 16, wherein said bulbous node applies pressure on said corresponding artery.

18. The method of claim 15, further comprising:

tightening the tourniquet to maintain pressure to said at least one hemorrhage control plate.

19. The method of claim 18, wherein said bulbous node maintains pressure on said corresponding artery.

20. A hemorrhage control system comprising:

a tourniquet configured to receive at least one hemorrhage control plate, said at least one hemorrhage control plate having a baseplate and a bulbous node extending outwardly from said baseplate, said bulbous node configured to be positioned against a patient's body such that said bulbous node aligns with an artery associated with said patient's body; and a first insert tab positioned at a first end of said baseplate, a second insert tab positioned at a second end of said baseplate, said second end opposite said first end, wherein said first insert tab is configured to mate with a corresponding first slot in the tourniquet and said second insert tab is configured to mate with a corresponding second slot in the tourniquet.

21. The hemorrhage control system of claim 20, wherein said bulbous node is configured to apply and maintain pressure on said artery when the tourniquet is tightened.

22. The hemorrhage control system of claim 20, wherein at least one of the first insert tab and the second insert tab further comprises a locking end spur.

23. A hemorrhage control system comprising:

a tourniquet configured to receive at least one hemorrhage control plate, said at least one hemorrhage control plate having a baseplate and a bulbous node extending outwardly from said baseplate, said bulbous node configured to be positioned against a patient's body such that said bulbous node aligns with an artery associated with said patient's body, wherein the baseplate is configured to bend temporarily and become arcuate when said first and second insert tabs are mated with said corresponding first and second slots in the tourniquet.

24. The hemorrhage control system of claim 23, wherein said bulbous node is configured to apply and maintain pressure on said artery when the tourniquet is tightened.

* * * * *